(12) United States Patent
Kang

(10) Patent No.: US 10,918,859 B2
(45) Date of Patent: Feb. 16, 2021

(54) RESISTIVE ELECTRIC TRANSFER BASED HIGH FREQUENCY MASSAGE DEVICE WITH SUCTION FUNCTION

(71) Applicant: Sun Young Kang, Seoul (KR)

(72) Inventor: Sun Young Kang, Seoul (KR)

(73) Assignee: SHENB CO., LTD., Seoul (KR)

( * ) Notice: Subject to any disclaimer, the term of this patent is extended or adjusted under 35 U.S.C. 154(b) by 289 days.

(21) Appl. No.: 16/108,029

(22) Filed: Aug. 21, 2018

(65) Prior Publication Data

US 2019/0111252 A1 Apr. 18, 2019

(30) Foreign Application Priority Data

Oct. 13, 2017 (KR) .......................... 10-2017-0133177

(51) Int. Cl.
*A61N 1/32* (2006.01)
*A61B 18/12* (2006.01)
(Continued)

(52) U.S. Cl.
CPC .............. *A61N 1/322* (2013.01); *A61B 18/12* (2013.01); *A61B 18/1206* (2013.01);
(Continued)

(58) Field of Classification Search
CPC .......... A61N 1/322; A61N 1/06; A61N 1/328; A61N 1/36014; A61N 1/403; A61N 1/08;
(Continued)

(56) References Cited

U.S. PATENT DOCUMENTS

2004/0030329 A1\* 2/2004 Hagg ................. A61B 18/1206
606/38
2017/0189670 A1\* 7/2017 Brunson .............. A61N 1/0472
(Continued)

FOREIGN PATENT DOCUMENTS

JP 2005-125075 A 5/2005
JP 2015-532178 A 11/2015
(Continued)

OTHER PUBLICATIONS

Translation of KR 101648362. (Year: 2016).\*
Translation of KR 2017/0068697 (Year: 2017).\*
Translation of KR 2005/0080215 (Year: 2005).\*

*Primary Examiner* — Kendra D Carter
*Assistant Examiner* — Paige Kathleen Bugg
(74) *Attorney, Agent, or Firm* — Patent Office of Dr. Chung Park

(57) ABSTRACT

The present disclosure provides a resistive electric transfer (RET)-based high-frequency massaging device with a suction function, the device comprising: a main body including an upper cover and a lower cover having a suction hole defined in a bottom center thereof; a plurality of electrode pads arranged on a bottom outer face of the lower cover in a circumferentially; a high-frequency generator mounted on the lower cover; a suction channel assembly communicating with the suction-hole defined in the lower cover; a suction motor operatively connected to the suction channel assembly; and a controller configured to control the high frequency output from the high-frequency generator and suction-drive of the suction motor, wherein the plurality of electrode pads is configured such that adjacent electrode pads have alternating polarities.

11 Claims, 10 Drawing Sheets

(51) Int. Cl.
 *A61H 7/00*  (2006.01)
 *A61B 18/14*  (2006.01)
 *A61H 23/00*  (2006.01)
 *A61N 1/06*  (2006.01)
 *A61N 5/06*  (2006.01)
 *A61B 18/00*  (2006.01)
 *A61N 1/36*  (2006.01)
 *A61N 1/40*  (2006.01)

(52) U.S. Cl.
 CPC ......... *A61B 18/1402* (2013.01); *A61H 7/008* (2013.01); *A61H 23/00* (2013.01); *A61N 1/06* (2013.01); *A61N 1/328* (2013.01); *A61N 5/0616* (2013.01); *A61B 2018/0016* (2013.01); *A61B 2018/0047* (2013.01); *A61B 2018/00291* (2013.01); *A61B 2018/00464* (2013.01); *A61B 2018/00702* (2013.01); *A61B 2018/1226* (2013.01); *A61H 2201/0153* (2013.01); *A61H 2201/0157* (2013.01); *A61N 1/36014* (2013.01); *A61N 1/403* (2013.01); *A61N 5/0625* (2013.01); *A61N 2005/0644* (2013.01); *A61N 2005/0649* (2013.01); *A61N 2005/0651* (2013.01); *A61N 2005/0652* (2013.01); *A61N 2005/0659* (2013.01)

(58) Field of Classification Search
 CPC ...... A61N 1/3603; A61N 1/18; A61N 5/0616; A61N 5/0625; A61N 5/0644; A61N 2005/0644; A61N 2005/0649; A61N 2005/0651; A61N 2005/0652; A61N 2005/0659; A61B 18/12; A61B 18/1206; A61B 18/126; A61B 18/1402; A61B 2018/0016; A61B 2018/00291; A61B 2018/00464; A61B 2018/0047; A61B 2018/00702; A61B 2018/1226; A61B 2017/22079; A61B 2217/005; A61H 23/00; A61H 2201/0153; A61H 2201/0157; A61H 2201/10; A61H 2201/1683; A61H 9/00; A61H 9/005; A61H 9/0057; A61H 15/02; A61H 15/0085; B01D 46/00; B01D 46/10; B01D 46/0005; B01D 46/0008; B01D 46/2422; B01D 46/001; B01D 46/0012; B01D 46/0023; B01D 2267/40; B01D 2271/027; B01D 2273/30; B01D 2275/202; A61M 1/0056
 See application file for complete search history.

(56) References Cited

U.S. PATENT DOCUMENTS

2017/0252261 A1\* 9/2017 Khorassani Zadeh ..................... A61H 9/0057
2018/0161233 A1\* 6/2018 Nakanishi .......... A61H 15/0092

FOREIGN PATENT DOCUMENTS

| KR | 10-2005-0080215 A | | 8/2005 | |
| --- | --- | --- | --- | --- |
| KR | 20050080215 A | \* | 8/2005 | |
| KR | 10-1639207 B1 | | 7/2016 | |
| KR | 10-1648362 B1 | | 8/2016 | |
| KR | 101648362 B1 | \* | 8/2016 | |
| KR | 10-1697334 B1 | | 1/2017 | |
| KR | 10-2017-0068697 A | | 6/2017 | |
| KR | 20170068697 A | \* | 6/2017 | ............. A61B 17/50 |
| KR | 10-1770364 B1 | | 8/2017 | |
| KR | 10-1773508 B1 | | 8/2017 | |
| WO | 2017/038822 A1 | | 3/2017 | |

\* cited by examiner

【Figure 1】
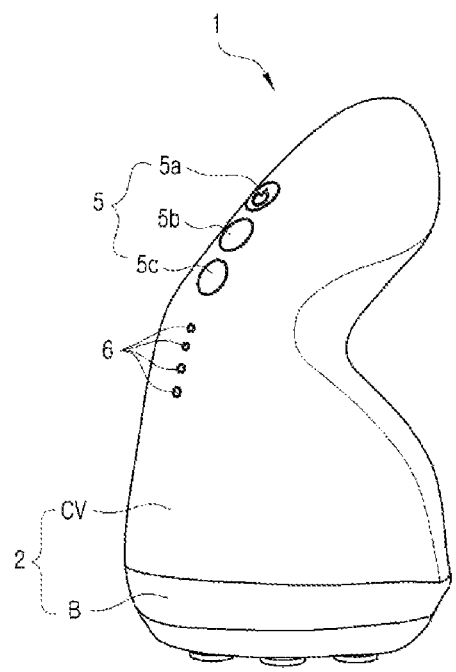
【Figure 2】
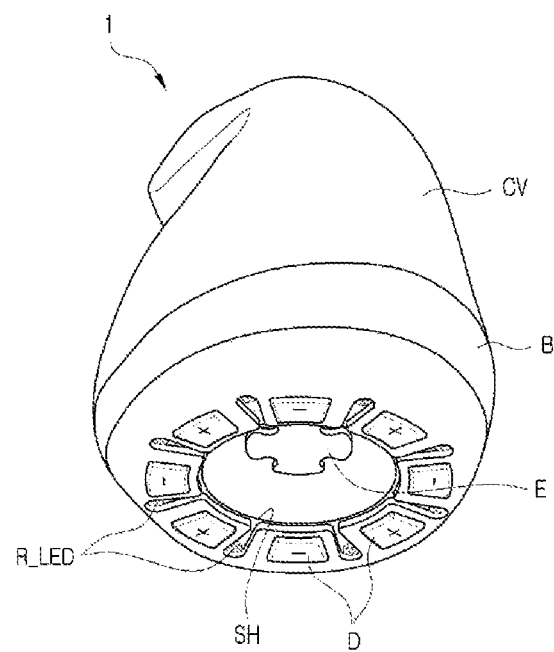

【Figure 3】
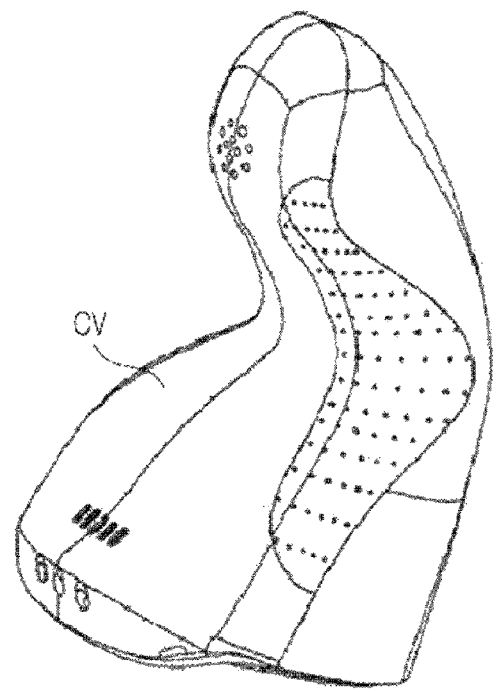
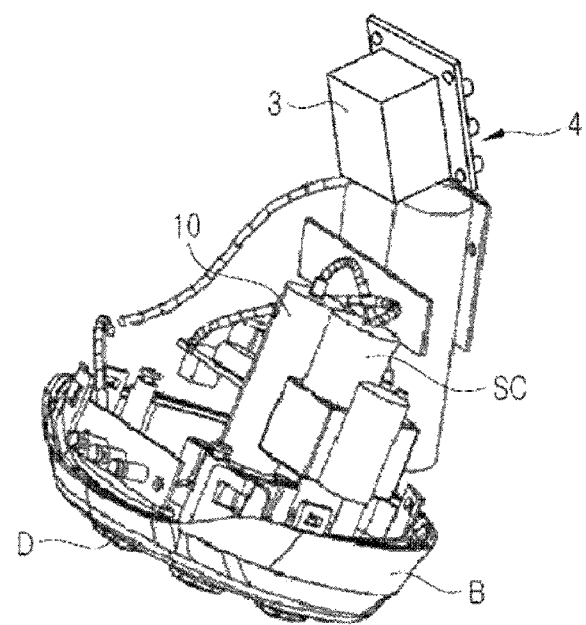

【Figure 4】
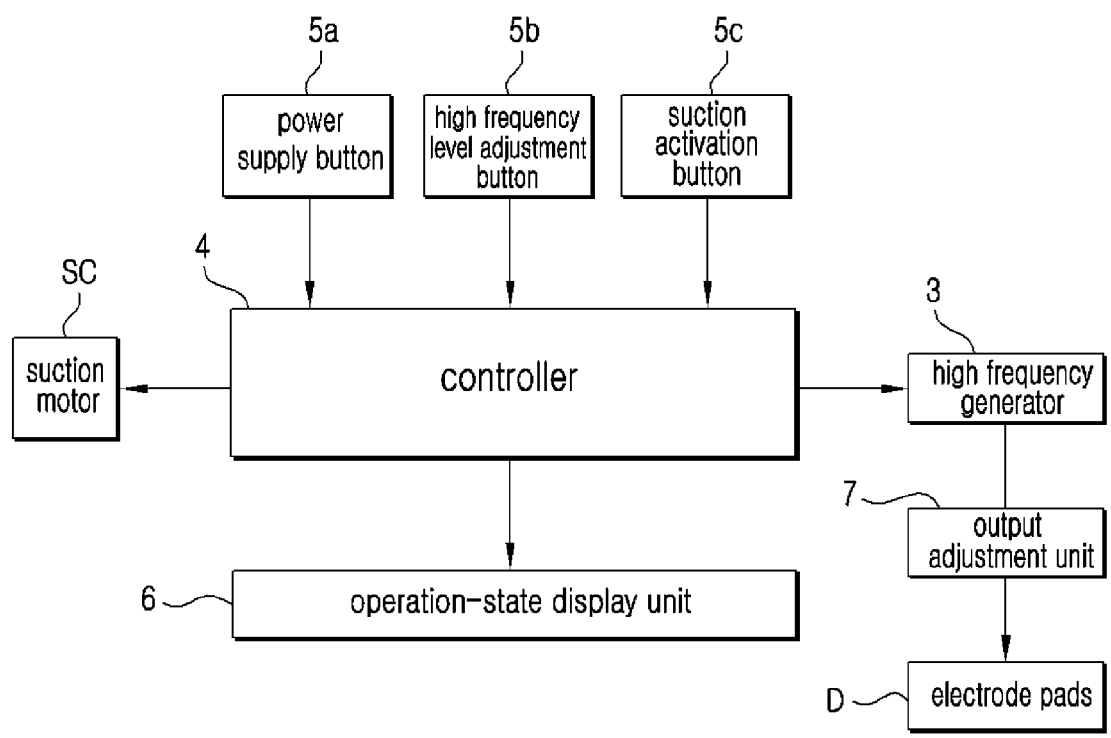

[Figure 5]
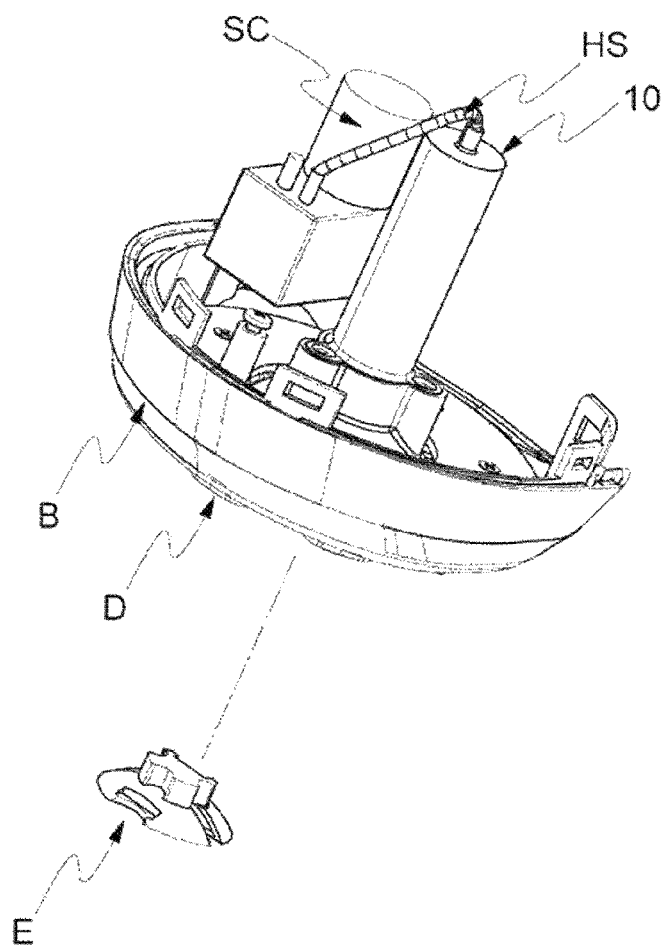

[Figure 6]
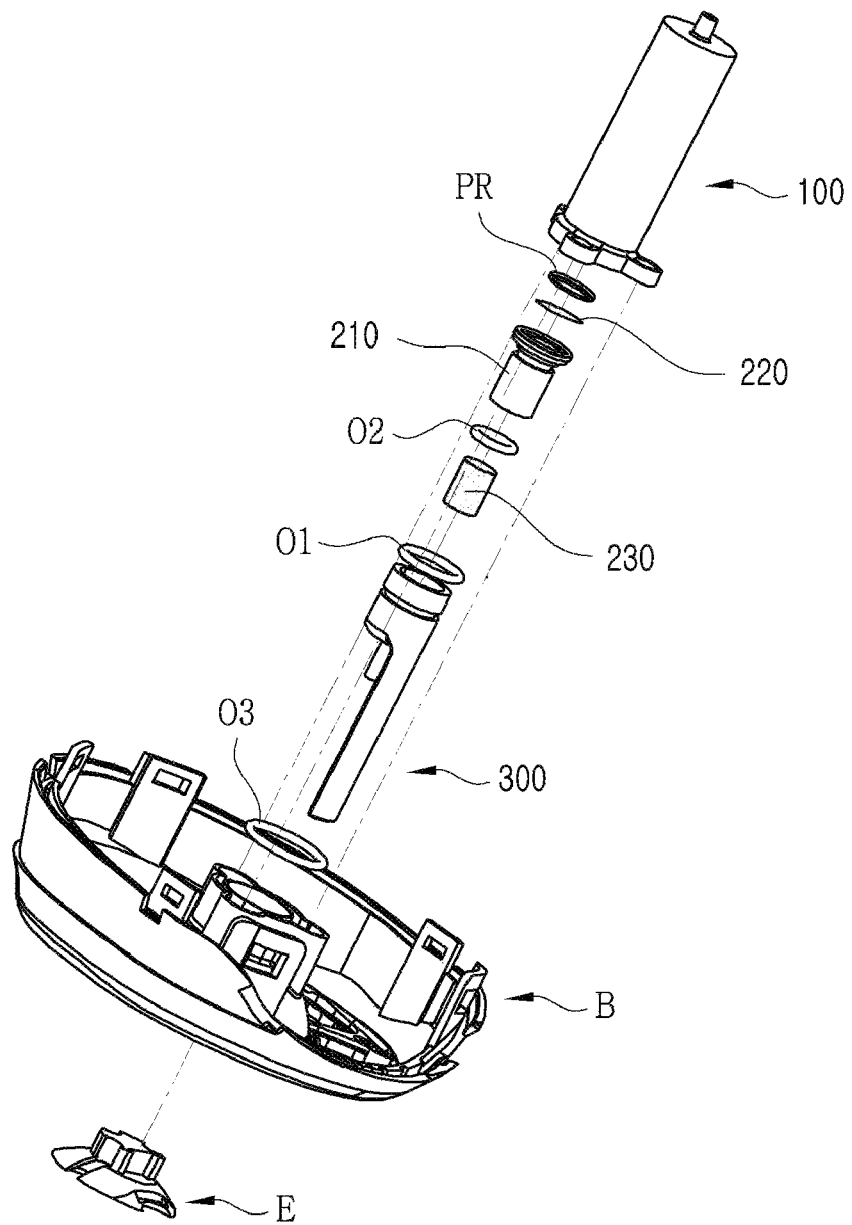

[Figure 7]
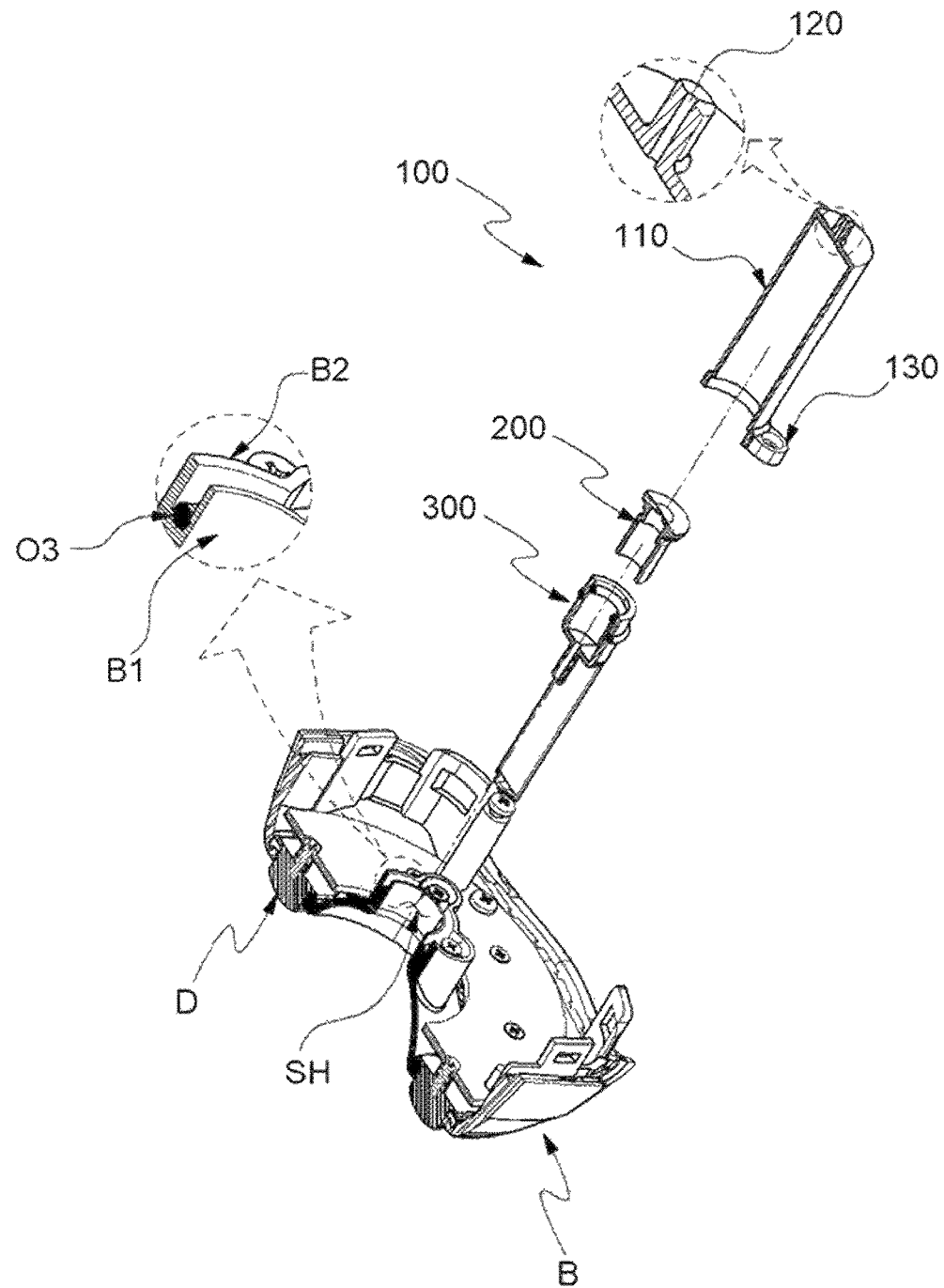

【Figure 8】
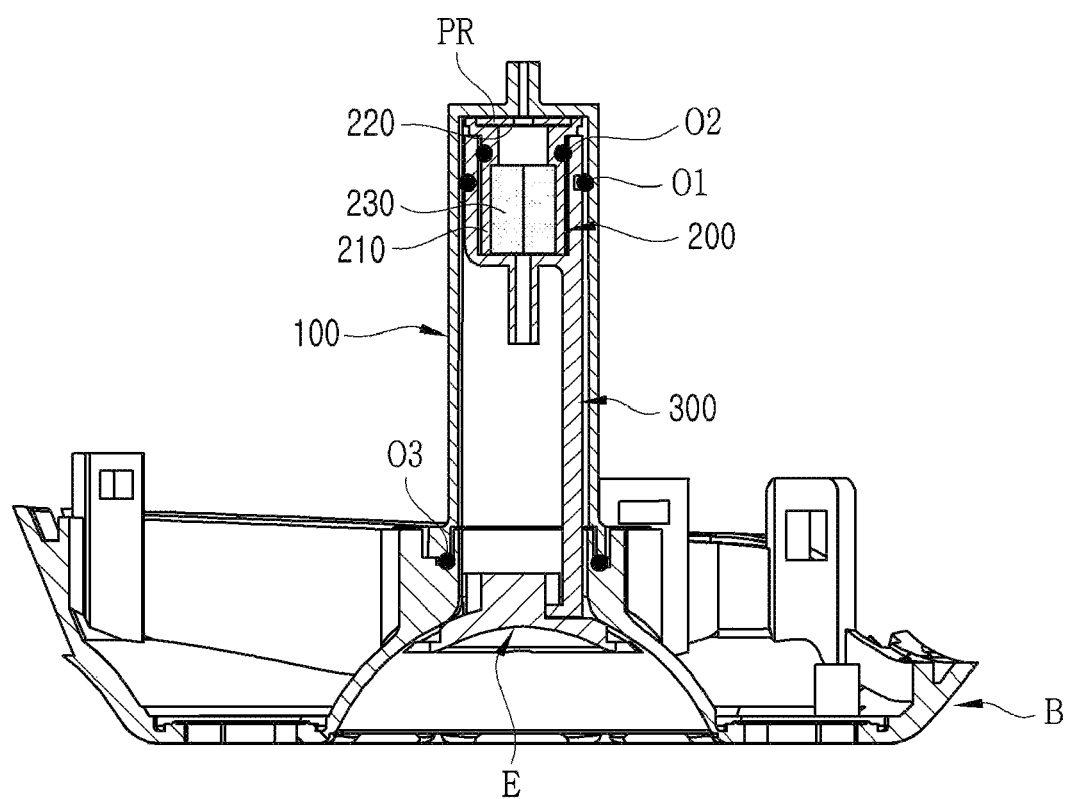

[Figure 9]
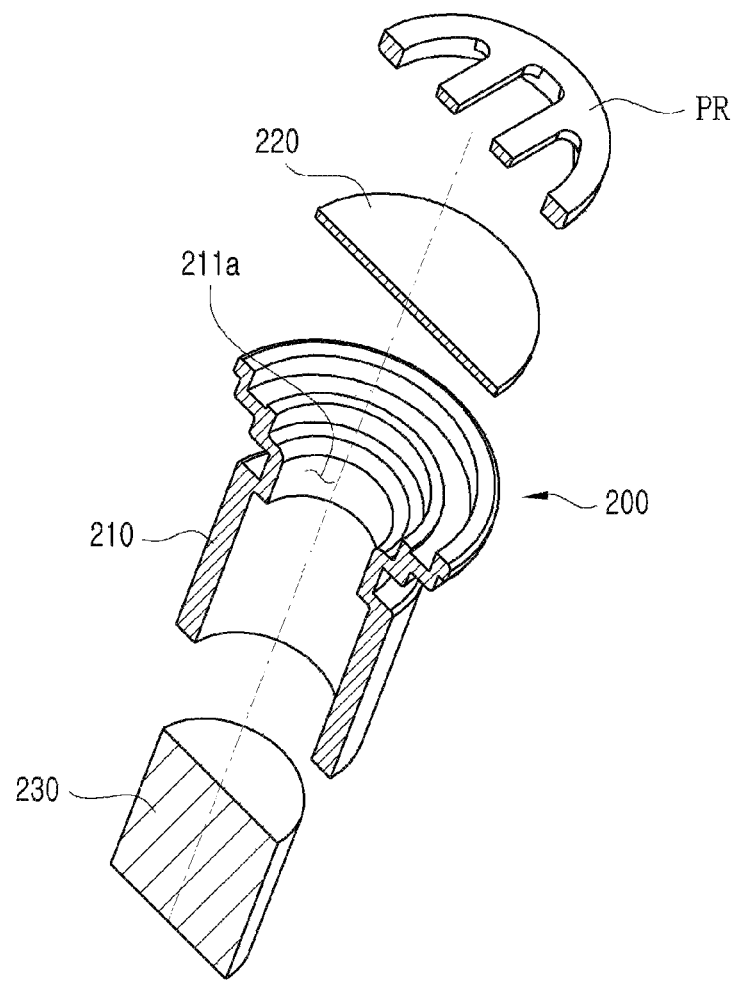

【Figure 10】
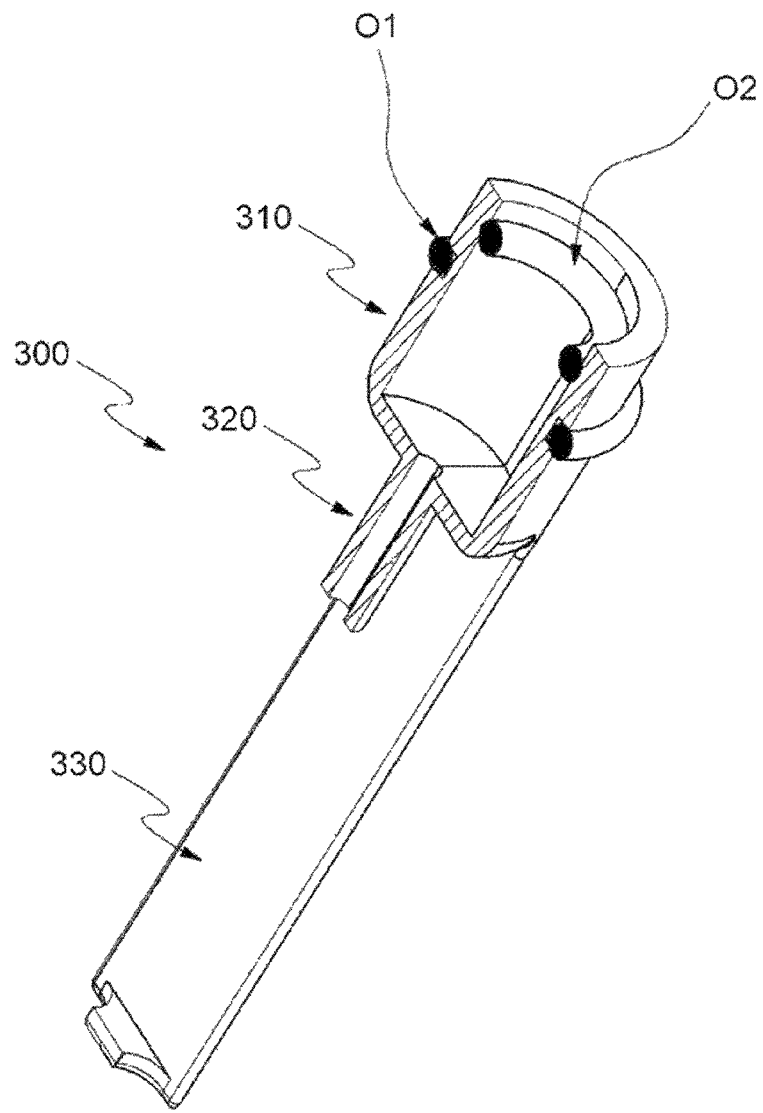

【Figure 11】
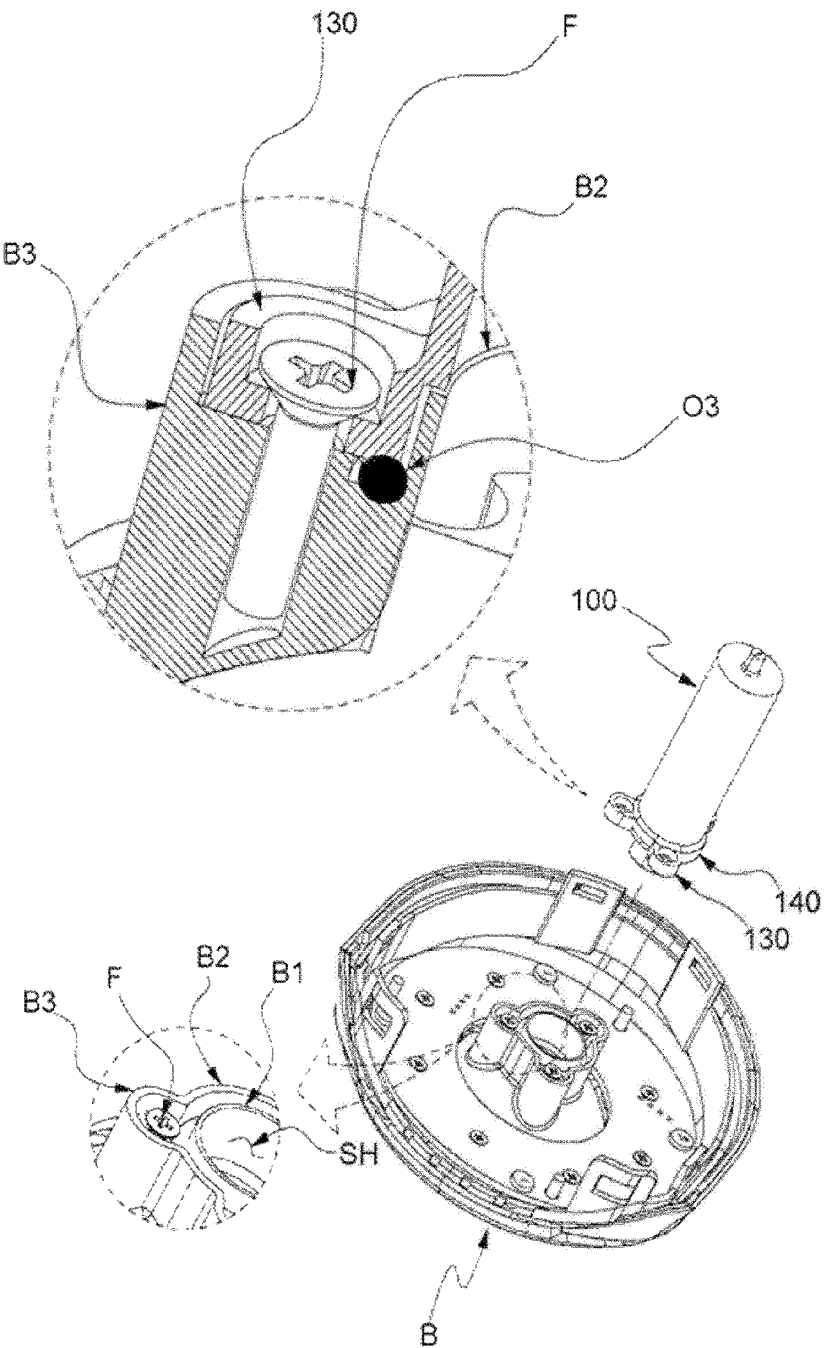

# RESISTIVE ELECTRIC TRANSFER BASED HIGH FREQUENCY MASSAGE DEVICE WITH SUCTION FUNCTION

BACKGROUND

Field of the Present Disclosure

The present disclosure release to a resistive electric transfer (RET)-based high-frequency massaging device with a suction function. More particularly, the present disclosure release to a resistive electric transfer (RET)-based high-frequency massaging device with a suction function, wherein stimulating of the deep part of the skin using high-frequency may lead to the decomposition of the fat layer by heat generation, while maximizing the massage effect by suctioning the skin, such that a combination of the suction function and the high-frequency effect may contribute to three-dimensional body management including the treatment of obesity, and may attain skin care and skin care effects such as skin elasticity enhancement.

Discussion of Related Art

Generally, the skin is on the outer surface of the body. The skin protects the internal organs from the outside in various directions and plays an important role in maintaining life and beauty. When such a skin loses its elasticity, it looks like sagging when it becomes loose. Thus, it is important to manage the skin normally.

In addition, in order to maintain skin aging and skin elasticity, a massage suitable for the skin condition of the user is required along with the cleansing of the skin, and the elasticity of the skin may be maintained through such massage to prevent aging.

Such skin massages include massaging in a variety of ways including hand massage, mechanical vibration based, far-infrared radiation based or high-frequency radiation based massage.

Recently, in one of the electric therapy methods applied to pain treatment and physical therapy in the medical field, many devices which are expected to have skin beauty and massage effect using high-frequency or low frequency have been proposed and released.

As life progresses with industrial development, interest in skin beauty, health, or body management is increasing. A variety of massagers have been introduced to reflect these demands. Most of them use capacitive electric transfer (CET) method, where it is difficult to deeply penetrate the skin and stimulate the skin epidermis. There are many devices that may perform only simple skin care and skin care. some devices are below expectation in that they do not perform simple skin care and skin care properly.

Meanwhile, as the eating habits are changed by the improvement of living, the obesity population is spreading a lot. In addition to genetic factors, environmental factors play an important role in recent obesity. Because obesity exacerbates health such as cardiovascular disease, people are trying to treat obesity through a variety of methods including obesity clinics. Further, three-dimensional body care and skin health are attracting attention.

Such an obesity treatment employs exercises, diet or drug therapy. Injection treatment such as fat decomposition injection, ultrasonic wave or liposuction is used for the purpose of body treatment. Various devices are used for this purpose.

PRIOR ART DOCUMENT

Patent Literature

Patent Document 1: Korean Patent No. 10-1639207
Patent Document 2: Korean Patent No. 10-1697334
Patent Document 3: Korean Patent No. 10-1770364
Patent Document 4: Korean Patent No. 10-1773508

SUMMARY

This Summary is provided to introduce a selection of concepts in a simplified form that are further described below in the Detailed Description. This Summary is not intended to identify all key features or essential features of the claimed subject matter, nor is it intended to be used alone as an aid in determining the scope of the claimed subject matter.

The present disclosure is based on solving the above problems and taking this into consideration. The present disclosure provides a resistive electric transfer (RET)-based high-frequency massaging device with a suction function. More particularly, the present disclosure provides a resistive electric transfer (RET)-based high-frequency massaging device with a suction function, wherein stimulating of the deep part of the skin using high-frequency may lead to the decomposition of the fat layer by heat generation, while maximizing the massage effect by suctioning the skin, such that a combination of the suction function and the high-frequency effect may contribute to three-dimensional body management including the treatment of obesity, and may attain skin care and skin care effects such as skin elasticity enhancement.

The present disclosure provides a resistive electric transfer (RET)-based high-frequency massaging device with a suction function, wherein a resistive electric transfer (RET)-based high-frequency massaging is combined with a suction function of the skin, wherein stimulating of the deep part of the skin using high-frequency based on the RET scheme may lead to the decomposition of the fat layer by heat generation, such that a combination of the suction function and the high-frequency massaging based on the RET may contribute to three-dimensional body management including the treatment of obesity, and may attain skin care and skin care effects such as skin elasticity enhancement.

The present disclosure provides a resistive electric transfer (RET)-based high-frequency massaging device with a suction function, wherein the user may grasp the device and apply the electrode pads of the device to various parts of the body such as abdomen, thigh and forearm of the user without pain, and, it is possible to reduce the fat layer located in the deep part of the skin by the high-frequency deeply penetrating into the skin and stimulation of the skin by the skin suction at the same time.

In a one aspect of the present disclosure, there is provided a resistive electric transfer (RET)-based high-frequency massaging device with a suction function, the device comprising: a main body including an upper cover and a lower cover, wherein the upper cover has a concave curved shape, and the lower cover is coupled to the upper cover and has a suction hole defined in a bottom center thereof; a plurality of electrode pads arranged on a bottom outer face of the lower cover in a circumferentially so as to be spaced apart from each other, wherein the electrode pads transmit a high frequency output onto a skin; a high-frequency generator mounted on the lower cover and configured to apply a high frequency to the plurality of electrode pads; a suction` channel assembly communicating with the suction-hole defined in the lower cover; a suction motor mounted on the lower cover and operatively connected to the suction channel assembly; and a controller configured to control the high frequency output from the high-frequency generator and suction-drive of the suction motor, wherein the plurality of electrode pads is configured such that adjacent electrode pads have alternating polarities, and, thus, polarities for the high frequency applied from the high-frequency generator are alternated, thereby to increase heat generation efficiency resulting from fat layer stimulation of the high frequency output in a deep portion of the skin, wherein sucking the skin via driving of the suction motor enhances skin elasticity via a massaging effect while enhancing thermal decomposition efficiency of a fat layer in a deep portion of the skin.

In one embodiment of the resistive electric transfer (RET)-based high-frequency massaging device, the controller includes: a control switch configured for adjusting a level of the high frequency output from the high-frequency generator and for adjusting an operation of the suction motor; and an operation-state display unit configured for displaying an operation state of the high-frequency massaging device, wherein the control switch includes: a power supply button configured for powering on or off the high-frequency massaging device; a high-frequency level adjustment button configured for adjusting the level of the high frequency output from the high-frequency generator; and a suction-activation button configured for operating the suction motor, wherein the operation-state display unit includes an operation indication LED configured to be turned on or off for an operation indication.

In one embodiment of the resistive electric transfer (RET)-based high-frequency massaging device, each of the electrode pads includes a single metal or an alloy having conductivity as a base material thereof, wherein a biocompatible trivalent chromium is coated on the base material, thereby to remove a trouble upon contact of each pad with the skin while softly and stably applying the high frequency output into the deep portion of the skin such that heat generation and fat decomposition efficiency resulting from stimulation of the fat layer is enhanced.

In one embodiment of the resistive electric transfer (RET)-based high-frequency massaging device, a noise filter is coupled to an output stage of the high-frequency generator, thereby to block generation of noise or remove the noise, wherein an output-adjustment unit includes a capacitor and a coil connected in series on the noise filter, wherein the output-adjustment unit allows a high frequency at a constant frequency to be outputted.

In one embodiment of the resistive electric transfer (RET)-based high-frequency massaging device, via operating of the high-frequency level adjustment button, the controller is configured to adjust an output voltage in multiple levels, wherein each time the high-frequency level adjustment button is pushed once, the output voltage increases by one level, wherein the output voltage at a highest level does not exceed 20% of a maximum output voltage, wherein via operating of the suction-activation button, a driving duration of the suction motor is adjusted in multiple levels by the controller, wherein the duration of the suction motor increases by one level per push of the suction-activation button, wherein at the highest level, continuous driving is set.

In one embodiment of the resistive electric transfer (RET)-based high-frequency massaging device, the suction channel assembly and the suction motor are connected through a connection hose such that the skin is sucked through the suction-hole by a suction pressure acting upon driving the suction motor, wherein the suction channel assembly includes a plurality of housings and multiple filters, such that when sucking the skin through the suction-hole using the suction pressure from the driving of the suction motor, the filters prevents liquid fluid from being sucked into the suction motor and thus prevents the suction motor from being damaged.

In one embodiment of the resistive electric transfer (RET)-based high-frequency massaging device, the suction channel assembly includes: a connection housing inserted in the suction-hole; a filter housing inserted into the connection housing and receiving the filters; and a guide housing constructed for housing the connection housing and the filter housing, wherein the connection housing includes: a hollow connection main body constructed for receiving the filter housing; a suction port extending downward from a bottom center of the connection main body and communicating with the connection main body, wherein the suction port has a pipe shape having a smaller diameter than a diameter of the main body; and a guide panel extending downward partially from a side wall of the connection main body and being integrally formed with the connection main body, wherein the guide panel is elongated such that a lower end of the guide panel is located inside the suction-hole, wherein when sucking the skin through the suction-hole, fluid that has passed through the suction-hole is stored in an inner space of the guide housing, while air is supplied through the suction port to the connection main body.

In one embodiment of the resistive electric transfer (RET)-based high-frequency massaging device, the filter housing includes: a filter-mounted portion disposed inside the connection main body of the connection housing, wherein the filter-mounted portion includes a hollow body communicating with the connection main body, wherein the filter-mounted portion has an elongate through-hole defined therein whose upper diameter is reduced compared to a lower diameter; a primary filter disposed inside the hollow body of the filter-mounted portion, wherein the primary filter primarily filters and blocks liquid fluid contained in air sucked-in through the suction port and into the connection main body and allows passage of the air; and a secondary filter disposed on a top of the through-hole of the filter-mounted portion, wherein the secondary filter secondarily filters and completely block the fluid and allows only air to pass therethrough even when the fluid passes through the primary filter due to a large amount of the fluid inflow.

In one embodiment of the resistive electric transfer (RET)-based high-frequency massaging device, the guide housing includes: a guide hollow main body having an internal space for storing therein fluid sucked through the suction-hole, wherein the guide body has a bottom opening, wherein the guide main body communicates with the suction-hole; an air suction portion protruding upward from a center of a top face of the guide main body, wherein the air suction portion communicates with an inner space of the guide main body and is connected to the suction motor through a connection hose; and fixing rings protruding outwardly from an outer face of a lower end of the guide main body, wherein the fixing rings are constructed for providing a stable fixing force for the guide main body.

In one embodiment of the resistive electric transfer (RET)-based high-frequency massaging device, the primary filter includes a nonwoven filter or a sponge filter, while the secondary filter is formed of polytetrafluoroethylene (PTFE)

sold under the trademark Teflon™ or waterproof-and-breathable fabric membrane sold under the trademark Gore-Tex™.

In one embodiment of the resistive electric transfer (RET)-based high-frequency massaging device, each of a plurality of infrared light-emitting diodes (LEDs) is disposed at a position corresponding to a position between adjacent electrode pads and is disposed on a bottom inner face of the lower cover to induce a ray therapy by irradiation of an infrared wavelength to the skin, thereby to provide skin elasticity enhancement and care effect, wherein the bottom portion of the lower cover is configured such that infrared rays emitted from the infrared LEDs are irradiated to the skin.

In one embodiment of the resistive electric transfer (RET)-based high-frequency massaging device, a push ring is disposed on the secondary filter on the top face of the filter-mounted portion, wherein the push ring is interposed between the filter housing and the guide housing, such that the secondary filter is firmly adhered to the filter-mounted portion, and, thus, the secondary filter is pressed and supported on the filter-mounted portion without being easily detached therefrom.

In accordance with the present disclosure, the resistive electric transfer (RET)-based high-frequency massaging may be combined with a suction function of the skin. Thus, stimulating of the deep part of the skin using high-frequency based on the RET scheme may lead to the decomposition of the fat layer by heat generation. That is, a combination of the suction function and the high-frequency massaging based on the RET may contribute to three-dimensional body management including the treatment of obesity, and may attain skin care and skin care effects such as skin elasticity enhancement. In this way, the high-frequency stimulus delivered to the fat layer of the deep part of the skin at the site of interest is transmitted to the deep part of the skin, thereby inducing vigorous molecular movement in the fat layer of the skin, and, thus, heat is generated therein. As a result, the heat generated by the molecular movement and resistance in the fat tissue induces the tissue activity in the fat layer and acts to decompose fat in the deep part of the skin.

Further, in accordance with the present disclosure, the suction function of the skin through the suction-hole, and, thus, pulling the skin tissue may constantly shrink and relax the peripheral connective tissue of the deep fat tissue of the skin. Thus, lymph may be smoothly circulated through contraction and relaxation of the fat layer. The waste may be easily discharged by the smooth circulation of the lymph. This acts to decompose and remove the fat layer. As a result, the high-frequency massaging device according to the present disclosure may maximize the decomposition and removal efficiency of the fat layer in the deep part of the skin through the simultaneous action of the high frequency output and the suction function. This device may be used for pain treatment and physiotherapy by penetrating deep skin through high frequency output only.

Moreover, in accordance with the present disclosure, the user may grasp the device and apply the electrode pads of the device to various parts of the body such as abdomen, thigh and forearm of the user without pain, and, it is possible to reduce the fat layer located in the deep part of the skin by the high-frequency deeply penetrating into the skin and stimulation of the skin by the skin suction at the same time.

BRIEF DESCRIPTION OF THE DRAWINGS

FIG. 1 is an external perspective view of a high-frequency massaging device according to an embodiment of the present disclosure.

FIG. 2 is a bottom perspective view of a high-frequency massaging device according to an embodiment of the present disclosure.

FIG. 3 is an exploded perspective view of a high-frequency massaging device according to an embodiment of the present disclosure, with the upper cover and the lower cover being separated from each other.

FIG. 4 is a block diagram showing an operational control relationship in the high-frequency massaging device according to the embodiment of the present disclosure.

FIG. 5 is a lumbar view showing the lower cover side of the high-frequency massaging device according to the embodiment of the present disclosure.

FIG. 6 is an exploded perspective view illustrating suction channel assembly in a high-frequency massaging device according to an embodiment of the present disclosure.

FIG. 7 is a cross-sectional exploded perspective view illustrating the suction channel assembly of a high-frequency massaging device according to an embodiment of the present disclosure.

FIG. 8 is a cross-sectional view to illustrate suction channel assembly of a high-frequency massaging device according to an embodiment of the present disclosure.

FIG. 9 is a cross-sectional exploded perspective view illustrating a filter housing of the suction channel assembly according to an embodiment of the present disclosure.

FIG. 10 is a cross-sectional perspective view illustrating the connection housing of the suction channel assembly according to an embodiment of the present disclosure.

FIG. 11 is a perspective view illustrating the coupling between the lower cover and the guide housing in a high-frequency massaging device according to an embodiment of the present disclosure.

DETAILED DESCRIPTIONS

For simplicity and clarity of illustration, elements in the figures are not necessarily drawn to scale. The same reference numbers in different figures denote the same or similar elements, and as such perform similar functionality. Also, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

It will be understood that when an element or layer is referred to as being "connected to", or "coupled to" another element or layer, it can be directly on, connected to, or coupled to the other element or layer, or one or more intervening elements or layers may be present. In addition, it will also be understood that when an element or layer is referred to as being "between" two elements or layers, it can be the only element or layer between the two elements or layers, or one or more intervening elements or layers may also be present.

Spatially relative terms, such as "beneath," "below," "lower," "under," "above," "upper," and the like, may be used herein for ease of explanation to describe one element or feature's relationship to another element s or feature s as illustrated in the figures. It will be understood that the spatially relative terms are intended to encompass different orientations of the device in use or in operation, in addition to the orientation depicted in the figures. For example, if the device in the figures is turned over, elements described as "below" or "beneath" or "under" other elements or features would then be oriented "above" the other elements or features. Thus, the example terms "below" and "under" can encompass both an orientation of above and below. The device may be otherwise oriented for example, rotated 90 degrees or at other orientations, and the spatially relative descriptors used herein should be interpreted accordingly.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In the following description, numerous specific details are set forth in order to provide a thorough understanding of the present disclosure. The present disclosure may be practiced without some or all of these specific details. In other instances, well-known process structures and/or processes have not been described in detail in order not to unnecessarily obscure the present disclosure.

The RET-based high-frequency massaging device 1 with the suction function according to the embodiment of the present disclosure, as shown in FIG. 1 to FIG. 11 includes a main body 2 including an upper cover CV and a lower cover B, wherein the upper cover CV has a concave curved shape, and the lower cover B is fastened to the upper cover CV and has a suction hole SH defined in a bottom center thereof; a plurality of electrode pads D arranged on a bottom face of the lower cover B in a circumferentially so as to be spaced apart from each other, wherein the electrode pads D transmit an high frequency output onto a skin; a high-frequency generator 3 mounted on the lower cover B and configured to apply a high frequency to the plurality of electrode pads D; a suction channel assembly 10 communicating with the suction-hole SH defined in the lower cover B; a suction motor SC mounted on the lower cover B and operatively connected to the suction channel assembly 10; and a controller 4 configured to control the high frequency output from the high-frequency generator 3 and suction-drive of the suction motor SC.

The plurality of electrode pads D have alternating polarities between adjacent electrode pads. By outputting alternate polarities for the high frequency applied through the high-frequency generator 3, heat generation efficiency resulting from the fat layer stimulation in the deep portion of the skin can be increased.

Each of the electrode pads D may include a single metal or an alloy having conductivity as a base material. By coating and surface-treating the biocompatible trivalent chromium on the base material for the addition of trivalent ions thereto, it is possible to remove the trouble from the contact with the skin while softly and stably applying the high frequency output into the deep portion of the skin. Further, heat generation and decomposition efficiency due to the stimulation of the fat layer may be enhanced.

The suction channel assembly 10 and the suction motor SC are connected through a connection hose HS. The skin is sucked through the suction-hole SH by the suction pressure acting upon driving the suction motor SC. By sucking the skin through the driving of the suction motor SC, the skin elasticity may be enhanced through the massaging effect while enhancing the thermal decomposition efficiency of the fat layer in the deep part of the skin.

The controller 4 includes a control switch 5 for adjusting the level of the high frequency output from the high-frequency generator 3 and adjusting the operation of the suction motor SC; and an operation-state display unit 6 for displaying an operation state of the high-frequency massaging device 1. The control switch 5 and the operation-state display unit 6 are disposed on the upper cover CV and exposed to the outside.

The control switch 5 includes a power supply button 5a for powering on or off the high-frequency massaging device 1; a high-frequency level adjustment button 5b for adjusting the level of the high frequency output from the high-frequency generator 3, and a suction-activation button 5c for operating the suction motor SC.

In this connection, when operating the high-frequency level adjustment button 5b, the controller 4 adjusts the output voltage in multiple steps while applying the high frequency output at a constant frequency. Each time the high-frequency level adjustment button 5b is pushed once, the output voltage increases step-by-step. However, the output does not exceed 20% of the maximum output voltage.

In this connection, since the AC voltage used by the consumer is typically 110V or 220V, the maximum output voltage will be 220V.

In this connection, when operating the high-frequency level adjustment button 5b, the high frequency output is constantly output while the output voltage may be adjusted to three levels, for example, 193V±20% at the first level, 205V±20% in the second level, and 220V±20% in the third level.

Further, at the time of operating the suction-activation button 5c, the driving of the suction motor SC is controlled in multiple steps through the control by the controller 4. The operation time of the suction motor gradually increases per each push of the suction-activation button 5c, and in the last step, the continuous driving may be set.

In this connection, when the suction-activation button 5c is operated, the suction motor may be driven in three steps. For example, in the first step, the operation is stopped for one second after the operation of one second; in the second step, the operation is stopped for one second after the operation for two seconds; the continuous operation is set for the third step.

The operation-state display unit 6 is configured to be turned on for an operation indication such as a use state. The unit 6 may include an operation indication LED.

An output-adjustment unit 7 may be connected to the output stage of the high-frequency generator 3. By connecting a noise filter to the output stage of the high-frequency generator 3, it is possible to block the generation of noise or remove the noise during high frequency output. Further, a capacitor and a coil are connected in series on the noise filter, so that a high frequency at a constant frequency is outputted. This allows the user to output the desired high frequency output at a constant frequency and remove the noise, thereby to ensure accurate output.

A battery is provided on the lower cover B to supply power necessary for the suction motor SC, the high-frequency generator 3, and the controller 4.

According to the present disclosure, the user contacts the electrode pads D on the body skin, such as the user's waist, thigh, or forearm, while holding the main body 2 by hand.

When the high-frequency level adjustment button 5b in the controller 4 is operated, a high-frequency may be output through the high-frequency output unit 3. In this output, the output voltage may be selectively output step by step. As a result, a high-frequency stimulus is delivered to the fat layer located at the deep part of the skin of interest.

In this way, the high-frequency stimulus delivered to the fat layer of the deep part of the skin at the site of interest is transmitted to the deep part of the skin, thereby inducing vigorous molecular movement in the fat layer of the skin, and, thus, heat is generated therein. As a result, the heat generated by the molecular movement and resistance in the fat tissue induces the tissue activity in the fat layer and acts to decompose fat in the deep part of the skin.

In this connection, the plurality of electrode pads D transmits a constant frequency, for example, a high frequency output of 0.5 MHz to the fat layer in the deep part of the skin.

The adjacent electrode pads D alternately output the polarities opposite to each other, so that they have a form of a sine wave output. Thus, it is possible to more actively induce the molecular movement in the fat tissue, thereby increasing the efficiency of heat generation and thereby the fat decomposition efficiency.

Accordingly, according to the present disclosure, a high-frequency, for example, an output of 0.5 MHz is applied using a plurality of electrode pads D applying alternating polarities, so that fat decomposition and removal is achieved. This may help in the treatment of obesity. Further, body slimming may be enabled by continuous use of this device. This provides the advantage of making a three-dimensional body.

Further, according to the present disclosure, when the suction motor SC is driven through the operation of the suction-activation button 5c, the controller 4 penetrates the high frequency output into the deep part of the skin through the high-frequency generator 3. At the same time as this stimulation, the skin is sucked through the suction-hole SH, thereby providing a massaging effect by skin suction.

In this connection, the suction function of the skin through the suction-hole SH, and, thus, pulling the skin tissue may constantly shrink and relax the peripheral connective tissue of the deep fat tissue of the skin. Thus, lymph may be smoothly circulated through contraction and relaxation of the fat layer. The waste may be easily discharged by the smooth circulation of the lymph. This acts to decompose and remove the fat layer.

As a result, the high-frequency massaging device 1 according to the present disclosure may maximize the decomposition and removal efficiency of the fat layer in the deep part of the skin through the simultaneous action of the high frequency output and the suction function. This device may be used for pain treatment and physiotherapy by penetrating deep skin through high frequency output only.

In addition, in accordance with the present disclosure, a plurality of infrared LEDs R_LED may be disposed respectively between the plurality of electrode pads D spaced apart from each other on disposed on the bottom inner surface of the lower cover B. Thereby, it is possible to induce the ray therapy by irradiation of the infrared wavelength and to provide skin elasticity enhancement and care effect. In this connection, the bottom portion of the lower cover is configured such that infrared rays emitted from the infrared LEDs are irradiated to the skin.

In this connection, the above-mentioned infrared LEDs (R_LED) have a function of enhancing the skin elasticity and care function by the light therapy. Further, by applying the infrared wavelength in the skin, the high frequency is more penetrated into the fat layer in the deep part of the skin. As a result, the heat generation efficiency in the fat tissue is further enhanced.

Further, according to the present disclosure, when sucking the skin through the suction-hole SH defined in the center thereof by using the suction pressure from the driving of the suction motor SC, oil or fluid of the skin is sucked together. Thus, it is possible to prevent the suction motor SC from being damaged by the sucked fluid via preventing the sucked fluid from being sucked into the suction motor SC. For this purpose, the suction channel assembly 10 may be configured to form a plurality of housing shapes having a multiple filter structure, as shown in FIGS. 5 to 11.

Specifically, the suction channel assembly 10 includes: a connection housing 300 inserted in the suction-hole SH, a filter housing 200 inserted into the connection housing 300 and receiving the filter, and a guide housing 100 for housing the connection housing 300 and the filter housing 20.

In this connection, a hollow tube B1 extending in the height direction of the lower cover B is formed around the suction-hole SH. The guide housing 100 is coupled to the hollow tube B1.

The connection housing 300 includes a hollow connection main body 310 for receiving the filter housing 200, and a suction port 320 extending downward from the bottom center of the main body 310 and communicating with the main body 310, wherein the suction port 320 has a pipe shape having a smaller diameter than the main body 310. The connection housing 300 includes a guide panel 330 extending downward from the side wall of the connection main body 310 and being integrally formed with the connection main body 310. The panel 330 is elongated such that the lower end of the guide panel 330 is located inside the suction-hole SH.

In this connection, when sucking the skin through the suction-hole SH, the fluid that has passed through the suction-hole SH is stored in the inner space of the guide housing 100, and the air is supplied to the connection main body 310.

A first O-ring O1 is provided on an outer side of the connection main body 310, and a second O-ring O2 is provided on an inner side of the connection main body 310 to achieve a sealing function.

The filter housing 200 includes a filter-mounted portion 210 disposed inside the connection main body 310 of the connection housing 300. The filter-mounted portion 210 is a hollow body that communicates with the connection main body 310. The filter-mounted portion 210 has a through-hole 211a whose upper diameter is reduced compared to the lower opening. A primary filter 230 is disposed inside the hollow body of the filter-mounted portion 210. The primary filter 230 primarily filters the fluid flowing as included in the air sucked in through the suction port 320 and into the connection main body 310. The secondary filter 220 is disposed on the upper side of the through-hole 211a of the filter-mounted portion 210. The secondary filter 220 secondarily filters the fluid to completely block the fluid and allows only air to pass therethrough even when a fluid passes through the primary filter 230 due to a large amount of the fluid inflow.

In this connection, the primary filter 230 may be a nonwoven filter or a sponge filter, and the secondary filter may be formed of polytetrafluoroethylene (PTFE) sold under the trademark Teflon™ or waterproof-and-breathable fabric membrane sold under the trademark Gore-Tex™.

In this connection, a push ring PR on the secondary filter 220 on the upper surface of the filter-mounted portion 210 is interposed between the filter housing 200 and the guide housing 100. As a result, the secondary filter 220 can be firmly adhered to the filter-mounted portion 210, so that the secondary filter 220 may be pressed and supported without being easily detached therefrom. The through-hole 211a formed in the filter-mounted portion 210 may vary in size as required. The secondary filter 220 is formed to cover the hole 211a.

The guide housing 100 has a guide main body 110. The guide main body 110 is a hollow body having an internal space for storing a fluid sucked through the suction-hole SH and having a lower opening structure. The guide main body 110 communicates with the suction-hole SH. The guide housing 100 has an air suction portion 120. The air suction portion 120 protrudes upward from the center of the upper surface of the guide main body 110. The air suction portion 120 communicates with the inner space of the guide main body 110 and is connected to a suction motor SC through a connection hose HS. A fixing ring 130 protrudes outward from the outer surface of the lower end of the guide main body 110. The fixing ring 130 is for providing a stable fixing force to the guide main body 110 via the fastening.

The lower end of the guide main body 110 communicates with the suction-hole SH in the lower cover B.

The fixing ring 130 may protrude outwardly on a protrusion 140 protruding in an annular shape around the lower side of the guide main body 110.

That is, the filter housing 200 and the connection housing 300 are installed inside the guide main body 110. Thus, the filter housing 200 and the connection housing 300 communicate with the suction-hole SH. The air sucked through the suction-hole SH flows through the filter housing 200 the connection housing 300 and then through the air suction portion 120 of the guide housing 100 and into the suction motor SC.

In this connection, the residual fluid sucked from the user's skin may be stored in the guide housing 100. The suction to the suction motor SC side is blocked by the filtering function.

Around the hollow tube B1 corresponding to the suction-hole SH, a plurality of ring-shaped receiving walls B3 are arranged at regular intervals in the circumferential direction.

A circular arc wall B2 having a specific curvature is connected between the circumferential direction of the receiving wall B3. That is, since the arc wall B2 is formed around the hollow tube B1, the diameter of the arc wall B2 is larger than that of the hollow tube B1. As shown in the figure, the receiving wall B3 has a ring shape, and a plurality of the receiving walls B3 are circumferentially arranged around the arc wall B2, and are spaced apart from each other at regular intervals.

The fixing ring 130 is seated in the receiving wall B3. The protrusion B1 is seated between the arc wall B2 and the hollow tube B1. A well-known fastening means F is installed on the bottom of the receiving wall B3 after passing through the fixing ring 130. With this configuration, the guide housing 100 and the lower cover B are fixed to each other.

In this connection, the suction port 320 of the connection housing 300 has a narrow diameter and, especially, has a diameter much smaller than the connection main body 310. Therefore, only air among the fluid and air as sucked into the guide housing 100 through the suction hole SH is sucked through the suction port 320 and is transferred to the suction motor through the air suction portion 120 of the guide housing 100.

However, the fluid sucked through the suction-hole SH is hardly sucked into the suction port 320, thereby being stored in inner space in the connection housing 300 and the inner space of the guide housing 100. This is because, as described above, the suction port 320 has a downwardly extending shape with a narrow diameter.

However, some of the fluids may be sucked through the suction port 320. In this case, the suction of the fluid into the suction motor SC is fundamentally interrupted by the primary filter 230 and the secondary filter 220 provided in the filter housing 200.

The guide panel 330 has a piece shape. The panel is elongated to extend downward into the interior of the suction-hole SH. The flow of the fluid and the air is guided by the guide panel 330, and the fluid and the air may be guided to the suction port 320 side.

Further, the hollow tube B1 of the lower cover B may be sealed by the closing cap E. A third O-ring O3 is provided between the bottom surface of the fixing ring 130 of the guide housing 100 and the bottom surface of the receiving wall B3, thereby achieving more complete sealing.

According to this configuration in accordance with the present disclosure, it is possible to completely block the inflow of fluid such as oil flowing from the skin into the suction motor SC side. Thus, the suction motor SC may be protected from the fluid. After the high-frequency massaging device 1 according to the present disclosure is used and stopped and, then, a fluid such as oil stored in the guide housing 100 flows into the filter housing 200, the filtering interrupts the fluid into the suction motor. As a result, the suction of the fluid to the suction motor SC side can be blocked, and the suction motor SC can be safely protected.

Further, according to the present disclosure, when the fluid is sucked into the suction channel assembly 10, and there is a space in the interior of the guide housing 100, a certain amount of fluid is stored in the space. Further, when the suction operation stops or the high-frequency massaging device 1 is removed from the skin, the fluid staying inside the guide housing 100 is discharged again. Thus, the fluid does not directly enter the suction motor SC.

Although the present disclosure has been described with reference to the accompanying drawings, those skilled in the art to which the present disclosure pertains will understand that the present disclosure may be made in other specific forms without departing from the spirit or essential characteristics thereof.

It is, therefore, to be understood that the embodiments described above are to be considered in all respects only as illustrative and not restrictive. The scope of the present disclosure described in the foregoing description is defined by the claims that follow. It is intended that all changes and modifications derived from the meaning and scope of the claims and their equivalents be construed as including the scope of the present disclosure.

What is claimed is:

1. A resistive electric transfer (RET)-based high-frequency massaging device with a suction function, the device comprising:
    a main body including an upper cover and a lower cover, wherein the upper cover has a concave curved shape, and the lower cover is coupled to the upper cover and has a suction hole defined in a bottom center thereof;
    a plurality of electrode pads arranged on a bottom outer face of the lower cover circumferentially so as to be spaced apart from each other, wherein the plurality of electrode pads transmit a high frequency output onto a skin;
    a high-frequency generator mounted on the lower cover and configured to apply a high frequency to the plurality of electrode pads;
    a suction channel assembly communicating with the suction-hole defined in the lower cover;
    a suction motor mounted on the lower cover and operatively connected to the suction channel assembly; and
    a controller configured to control the high frequency applied by the high-frequency generator and suction-drive of the suction motor;
    wherein the plurality of electrode pads is configured such that adjacent electrode pads have alternating polarities, and, thus, polarities for the high frequency applied from the high-frequency generator are alternated, thereby to increase heat generation efficiency resulting from fat layer stimulation of the high frequency output in a deep portion of the skin;
    wherein sucking the skin via driving of the suction motor enhances skin elasticity via a massaging effect while enhancing thermal decomposition efficiency of a fat layer in a deep portion of the skin;
    wherein the suction channel assembly includes:
    a connection housing inserted in the suction-hole;
    a filter housing inserted into the connection housing and receiving a plurality of filters; and
    a guide housing for housing the connection housing and the filter housing;
    wherein the connection housing includes:
    a hollow connection main body for receiving the filter housing;
    a suction port extending downward from a bottom center of the hollow connection main body and communicating with the hollow connection main body, wherein the suction port has a pipe shape having a smaller diameter than a diameter of the main body; and
    a guide panel extending downward partially from a side wall of the hollow connection main body and being integrally formed with the connection main body, wherein the guide panel is elongated such that a lower end of the guide panel is located inside the suction-hole;
    wherein, when sucking the skin through the suction-hole, fluid that has passed through the suction-hole is stored in an inner space of the guide housing, while air is supplied through the suction port to the connection main body.

2. The resistive electric transfer (RET)-based high-frequency massaging device of claim 1, wherein the controller includes:
    a control switch configured for adjusting a level of the high frequency applied by the high-frequency generator and for adjusting an operation of the suction motor; and
    an operation-state display unit configured for displaying an operation state of the high-frequency massaging device,
    wherein the control switch includes:
    a power supply button configured for powering on or off the high-frequency massaging device;
    a high-frequency level adjustment button configured for adjusting the level of the high frequency applied by the high-frequency generator; and
    a suction-activation button configured for operating the suction motor,
    wherein the operation-state display unit includes an operation indication LED configured to be turned on or off for an operation indication.

3. The resistive electric transfer (RET)-based high-frequency massaging device of claim 1, wherein each of the plurality of electrode pads includes a single metal or an alloy having conductivity as a base material thereof, wherein a biocompatible trivalent chromium is coated on the base material.

4. The resistive electric transfer (RET)-based high-frequency massaging device of claim 1, wherein a noise filter is coupled to an output stage of the high-frequency generator, thereby to block generation of noise or remove the noise, wherein an output-adjustment unit includes a capacitor and a coil connected in series on the noise filter, wherein the output-adjustment unit allows a high frequency at a constant frequency to be outputted.

5. The resistive electric transfer (RET)-based high-frequency massaging device of claim 2, wherein via operating of the high-frequency level adjustment button, the controller is configured to adjust an output voltage in multiple levels, wherein each time the high-frequency level adjustment button is pushed once, the output voltage increases by one level, wherein the output voltage at a highest level does not exceed 20% of a maximum output voltage,
    wherein via operating of the suction-activation button, a driving duration of the suction motor is adjusted in multiple levels by the controller, wherein the duration of the suction motor increases by one level per push of the suction-activation button, wherein at the highest level, continuous driving is set.

6. The resistive electric transfer (RET)-based high-frequency massaging device of claim 1, wherein the suction channel assembly and the suction motor are connected through a connection hose such that the skin is sucked through the suction-hole by a suction pressure acting upon driving the suction motor, wherein the suction channel assembly includes a plurality of housings and the plurality of filters, such that when sucking the skin through the suction-hole using the suction pressure from the driving of the suction motor, the plurality of filters prevent liquid fluid from being sucked into the suction motor and thus prevent the suction motor from being damaged.

7. The resistive electric transfer (RET)-based high-frequency massaging device of claim 1, wherein the filter housing includes:
   a filter-mounted portion disposed inside the hollow connection main body of the connection housing, wherein the filter-mounted portion includes a hollow body communicating with the hollow connection main body, wherein the filter-mounted portion has an elongate through-hole defined therein whose upper diameter is reduced compared to a lower diameter;
   a primary filter disposed inside the hollow body of the filter-mounted portion, wherein the primary filter primarily filters and blocks liquid fluid contained in air sucked-in through the suction port and into the connection main body and allows passage of the air; and
   a secondary filter disposed on a top of the through-hole of the filter-mounted portion, wherein the secondary filter secondarily filters and completely blocks the fluid and allows only air to pass therethrough even when the fluid passes through the primary filter due to a large amount of a fluid inflow.

8. The resistive electric transfer (RET)-based high-frequency massaging device of claim 1, wherein the guide housing includes:
   a guide hollow main body having an internal space for storing fluid sucked through the suction-hole, wherein the guide hollow main body has a bottom opening, wherein the guide hollow main body communicates with the suction-hole;
   an air suction portion protruding upward from a center of a top face of the guide hollow main body, wherein the air suction portion communicates with an inner space of the guide hollow main body and is connected to the suction motor through a connection hose; and
   fixing rings protruding outwardly from an outer face of a lower end of the guide hollow main body, wherein the fixing rings are constructed for providing a stable fixing force for the guide hollow main body.

9. The resistive electric transfer (RET)-based high-frequency massaging device of claim 7, wherein the primary filter includes a nonwoven filter or a sponge filter, while the secondary filter is formed of polytetrafluoroethylene (PTFE) or a waterproof-and-breathable fabric membrane.

10. The resistive electric transfer (RET)-based high-frequency massaging device of claim 1, wherein each of a plurality of infrared light-emitting diodes (LEDs) is disposed at a position corresponding to a position between adjacent electrode pads and is disposed on a bottom inner face of the lower cover to induce a ray therapy by irradiation of an infrared wavelength to the skin, thereby to provide care effect by skin elasticity enhancement,
   wherein a bottom portion of the lower cover is configured such that infrared rays emitted from the infrared LEDs are irradiated to the skin.

11. The resistive electric transfer (RET)-based high-frequency massaging device of claim 7, wherein a push ring is disposed on the secondary filter on a top face of the filter-mounted portion, wherein the push ring is interposed between the filter housing and the guide housing, such that the secondary filter is firmly adhered to the filter-mounted portion, and, thus, the secondary filter is pressed and supported on the filter-mounted portion without being easily detached therefrom.

\* \* \* \* \*